(12) United States Patent
Lerner

(10) Patent No.: US 10,136,971 B2
(45) Date of Patent: Nov. 27, 2018

(54) POSITIONING JIG AND IMPROVED METHODS TO DESIGN AND MANUFACTURE DENTAL IMPLANTS

(71) Applicant: Todd H. Lerner, Port Washington, NY (US)

(72) Inventor: Todd H. Lerner, Port Washington, NY (US)

( * ) Notice: Subject to any disclaimer, the term of this patent is extended or adjusted under 35 U.S.C. 154(b) by 0 days.

(21) Appl. No.: 15/724,913

(22) Filed: Oct. 4, 2017

(65) Prior Publication Data

US 2018/0021112 A1 Jan. 25, 2018

Related U.S. Application Data

(62) Division of application No. 14/362,237, filed as application No. PCT/US2012/067308 on Nov. 30, 2012.

(60) Provisional application No. 61/565,649, filed on Dec. 1, 2011.

(51) Int. Cl.
| | |
|---|---|
| A61C 19/00 | (2006.01) |
| A61C 11/08 | (2006.01) |
| A61C 1/08 | (2006.01) |
| A61C 13/083 | (2006.01) |
| A61C 13/087 | (2006.01) |
| A61C 11/00 | (2006.01) |
| A61C 13/34 | (2006.01) |
| A61C 13/00 | (2006.01) |

(52) U.S. Cl.
CPC ............ *A61C 11/087* (2013.01); *A61C 1/084* (2013.01); *A61C 11/001* (2013.01); *A61C 11/003* (2013.01); *A61C 11/08* (2013.01); *A61C 13/00* (2013.01); *A61C 13/083* (2013.01); *A61C 13/087* (2013.01); *A61C 13/34* (2013.01); *Y10T 29/49567* (2015.01)

(58) Field of Classification Search
CPC ..... A61C 11/087; A61C 11/003; A61C 11/08; A61C 11/001; A61C 13/00; A61C 13/34; A61C 13/087; A61C 13/083; A61C 1/084; Y10T 29/49567
USPC ....................................... 433/34, 49–67, 213
See application file for complete search history.

(56) References Cited

U.S. PATENT DOCUMENTS

| 4,055,896 A | 11/1977 | Corbett | |
|---|---|---|---|
| 4,174,570 A * | 11/1979 | Schwartz | A61C 9/002 269/8 |

(Continued)

FOREIGN PATENT DOCUMENTS

WO 02058581 A2 8/2002

OTHER PUBLICATIONS

International Search Report and Written Opinion dated Mar. 19, 2013, from related International Application No. PCT/US2012/067308.

*Primary Examiner* — Matthew Nelson
(74) *Attorney, Agent, or Firm* — Olive Law Group, PLLC; Nathan P. Letts

(57) ABSTRACT

This invention is directed to a positioning jig for preparing a two or more of adjacent teeth for a dental prosthesis comprising a member with (i) three or more parallel bores in the member and (ii) one or more means to attach the member to a dental articulator. The invention is also directed to methods of use of the position jig such as to prepare a series of aligned holes in teeth or aligned holes mockup of a dental bridge for a prosthesis.

20 Claims, 20 Drawing Sheets

(56) References Cited

U.S. PATENT DOCUMENTS

Figure 1:
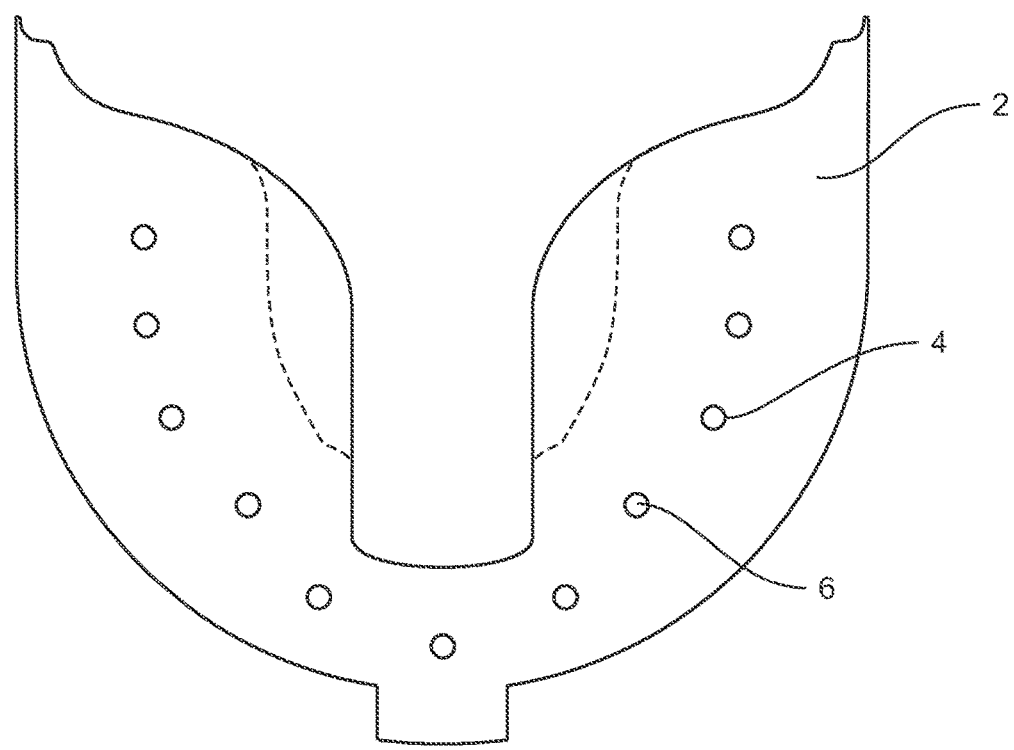

| | | | | |
|---|---|---|---|---|
| 5,749,725 A * | 5/1998 | Chinlund | ............... | A61C 11/08 |
| | | | | 433/60 |
| 6,471,513 B1 * | 10/2002 | Huffman | ................ | A61C 9/002 |
| | | | | 433/34 |
| 6,582,931 B1 | 6/2003 | Kois et al. | | |
| 7,322,821 B1 * | 1/2008 | Lin | ........................ | A61C 1/084 |
| | | | | 433/201.1 |
| 8,529,255 B2 * | 9/2013 | Poirier | ................... | A61C 1/084 |
| | | | | 433/72 |
| 2002/0102514 A1 * | 8/2002 | Huffman | ................ | A61C 9/002 |
| | | | | 433/34 |
| 2004/0013999 A1 * | 1/2004 | Sussman | .............. | A61B 17/176 |
| | | | | 433/75 |
| 2006/0292519 A1 * | 12/2006 | Bianchetto Buccia | ...................... | |
| | | | | A61C 9/002 |
| | | | | 433/34 |
| 2009/0017418 A1 * | 1/2009 | Gittelson | ............... | A61C 1/084 |
| | | | | 433/75 |

* cited by examiner

POSITIONING JIG AND IMPROVED METHODS TO DESIGN AND MANUFACTURE DENTAL IMPLANTS

CROSS REFERENCE TO RELATED APPLICATIONS

This application is a divisional of U.S. patent application Ser. No. 14/362,237 which was a 35 U.S.C. 371 application of International PCT Patent Application No. PCT/US12/67308, filed on Nov. 30, 2012 which claims the benefit of U.S. Provisional Patent Application No. 61/565,649, filed Dec. 1, 2011; the contents of which are hereby incorporated by reference herein in their entireties.

1. FIELD OF THE INVENTION

This invention relates a positioning jig for aligning the holes in artificial denture teeth in an artificial tooth arrangement (ATA) for replacing a plurality of teeth. The invention also relates to methods of design and methods of manufacture of dental implants in general, particularly for making hybrid prostheses.

2. BACKGROUND OF THE INVENTION

2.1. Introduction

For patients who have lost many adjacent teeth, dental prostheses are widely used. These prostheses may be either removable full or partial dentures or fixed full or partial dentures. A common type of fixed denture is the "hybrid prosthesis" a term generally used to describe a wide variety of dental prostheses with materials of different composition. Specifically, denture teeth may be porcelain, plastic, or composite; denture may be acrylic or metal; and the denture may be fixed to a metal framework which is screwed into the jaw.

The term "hybrid prostheses" includes: the Branemark hybrid prosthesis; a fixed detachable prosthesis; a fixed hybrid prosthesis; a fixed-detachable implant-supported prosthesis; implant hybrid overdenture; and the hybrid prosthesis. These hybrid prostheses have a high rate of mechanical complications. In particular, based on a literature survey, Goodacre et al. reported the following complication rates: overdenture loss of retention/adjustment, 30%; esthetic veneer fracture (resin), 22%; overdenture relines, 19%; overdenture clip/attachment fracture, 17%; and esthetic veneer fracture (porcelain), 14%. Goodacre et al., 2003 *J Prosthetic Dent* 90(2) 121-132, "Clinical Complications with implants and Implant Prostheses." Basically, whether resin or porcelain, the teeth are breaking off. Other mechanical complications include: the fracture of the resin support; fracture of attachment to underlying metal framework; or the fracture of the metal framework/implant bar.

The reasons for these mechanical complications are many. Specific reasons for failure include the fact that the classical hybrid framework was a flat platform to support denture teeth. They were not designed with individualized metal supports for denture teeth. There also was almost no vertical support component on the lingual to prevent fracture of teeth distal to the last implant. Taylor and Bergman, *Laboratory Techniques for the Branemark System* 1990, Quintessence. In some designs, the heat processed acrylic was retained by acrylic beads which in many cases were covered with an opaque agent that may contribute to the failure. In some cases, the acrylic was wrapped around the implant bar for additional retention.

Another prosthesis design was described by Beumer and Lewis in 1989, Beumer and Lewis, *The Branemark Implant System, Clinical and Laboratory Procedures,* 1989; Ishiyaku, EuroAmerical, Inc.; Lewis et al. 1989, *Int J Oral Maxillofac Implants* 4(2): 147-52 "The restoration of improperly inclined osseointegrated implants." Their design actually gave individual support for the denture teeth but the rods were not parallel with each other. Furthermore, the teeth were added in sections with silicone matrices which are difficult to work with. In particular, it is difficult to get the denture teeth to maintain their position in the silicone matrices. Like the classical hybrid framework above, the vertical support component to the framework was insufficient. Additional vertical support would allow for greater structural durability. In this system, the lingual area was purposely left open to allow flasking like a partial denture as the heat processed acrylic resin needs a way to flow in. Another issue with this technique is that some of the teeth may change position in the flask once the wax is eliminated.

A number of ways to reduce the likelihood of fracture have been considered by the dental community. These ideas include: increasing the thickness of the veneer materials; the thickness of the acrylic denture teeth; and the thickness of the heat-cured denture resins; changing the framework such as the type of metal or fabrication; adding retentive elements to the framework; increasing the thickness of the framework; or mechanical chemical treatments of the framework.

Another complication with making improved hybrid frameworks is that each tooth must be individually drilled and individually fitted onto a post supporting the tooth in the denture material. This requires great precision and is extremely time consuming.

In summary, there is a long-felt need for techniques to make improved fixed or removable dentures or overdentures for a plurality of teeth.

3. SUMMARY OF THE INVENTION

In particular non-limiting embodiments, the invention provides a positioning jig for preparing two or more adjacent teeth for a dental prosthesis comprising: a member with (i) three or more parallel bores in the member; and (ii) one or more means for attaching the member to a dental articulator.

The invention also provides a method of preparing an artificial prosthesis having two or more adjacent teeth which comprises: preparing an artificial tooth arrangement (ATA) with two or more adjacent teeth in a mold on a positioning jig comprising a member with (i) three or more parallel bores in the member and (ii) one or more means for attaching the member to a dental articulator; placing at least three rigid struts in the parallel bores of the positioning jig; using at least one of the rigid struts to align a drill; drilling an aligned hole into each of the teeth in the mold; placing a rod in each of the aligned holes of the teeth to form a series of aligned rods; using the teeth and the aligned rods to prepare a dental mockup; copying the dental mockup to prepare a dental bridge; and affixing the teeth using the aligned holes to the dental bridge so as to prepare the artificial prosthesis.

Moreover, the invention provides a method of preparing a dental mockup with two or more aligned holes which comprises: preparing an artificial tooth arrangement (ATA) with two or more adjacent teeth in a mold on a positioning jig comprising a member with (i) three or more parallel bores in the member, and (ii) one or more means for attaching the member to a dental articulator; placing at least three rigid struts in the parallel bores of the positioning jig;

using at least one of the rigid struts to align a drill; drilling an aligned hole into each of the teeth in the mold; placing a rod in each of the aligned holes of the teeth to form a series of aligned rods; and using the teeth and the aligned rods to prepare the dental mockup with the plurality of aligned holes.

In addition, the invention provides a kit which comprises a positioning jig for preparing two or more adjacent teeth for a dental prosthesis comprising a member with (i) three or more parallel bores in the member and (ii) one or more means for attaching the member to a dental articulator; and three or more rigid struts with a diameter so they fit tightly in the parallel bores.

4. BRIEF DESCRIPTION OF THE FIGURES

FIG. 1 shows the positioning jig 2 with a plurality of bores 4, 6 of two different diameters.

Figure 2:
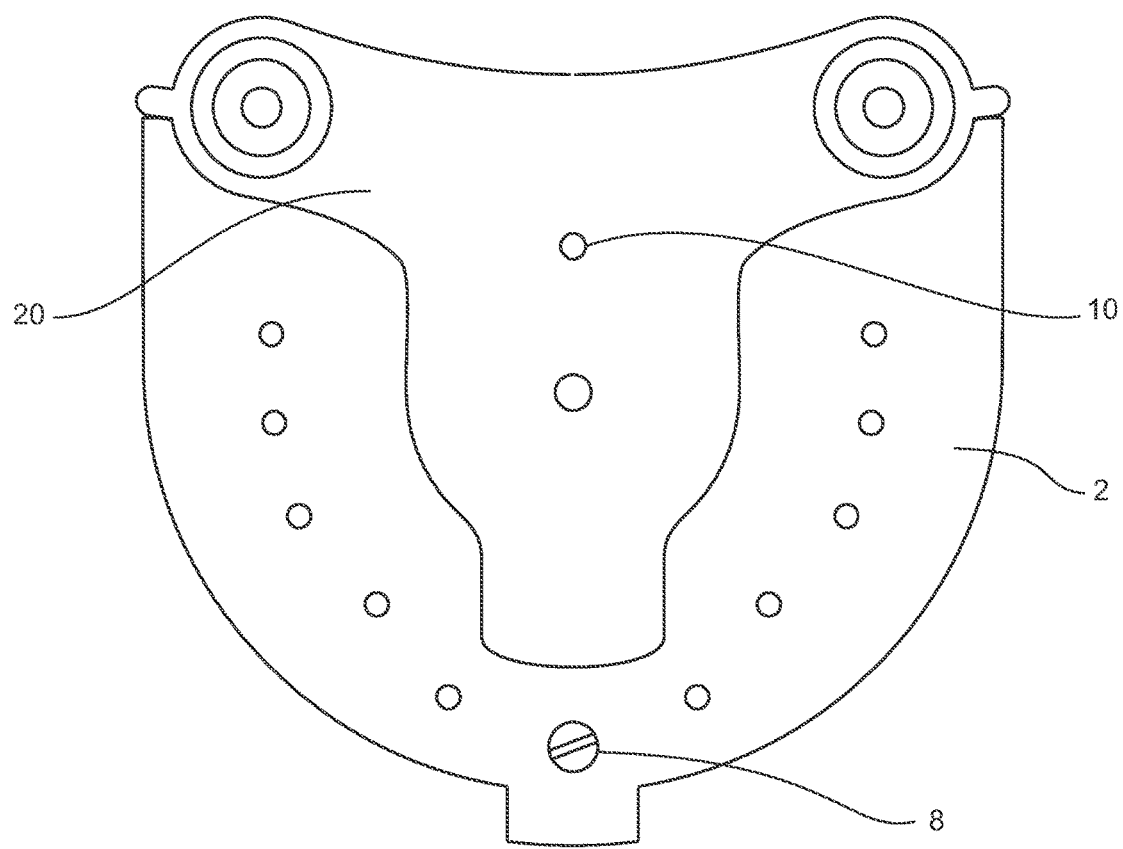

FIG. 2 shows an angled view of the positioning jig 2 firmly attached by screw 8 and pin 10 to the base of an articulator 20.

Figure 3:
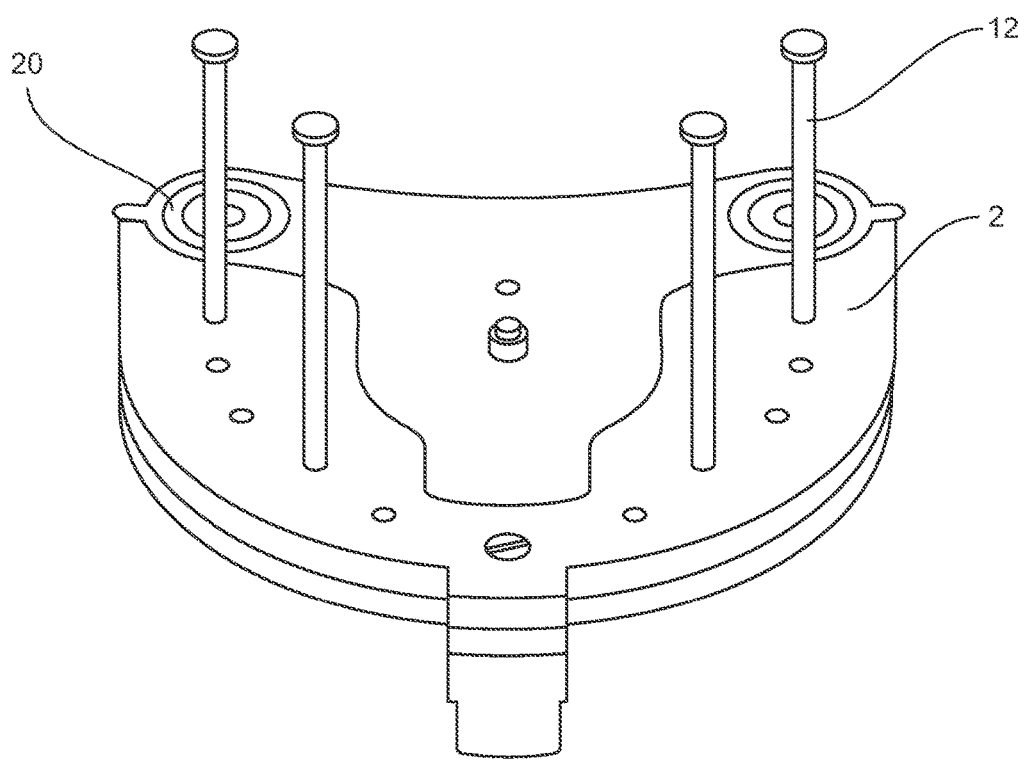

FIG. 3 shows rigid struts 12 placed in the bores of the positioning jig 2 mounted on the base of an articulator 20.

Figure 4:
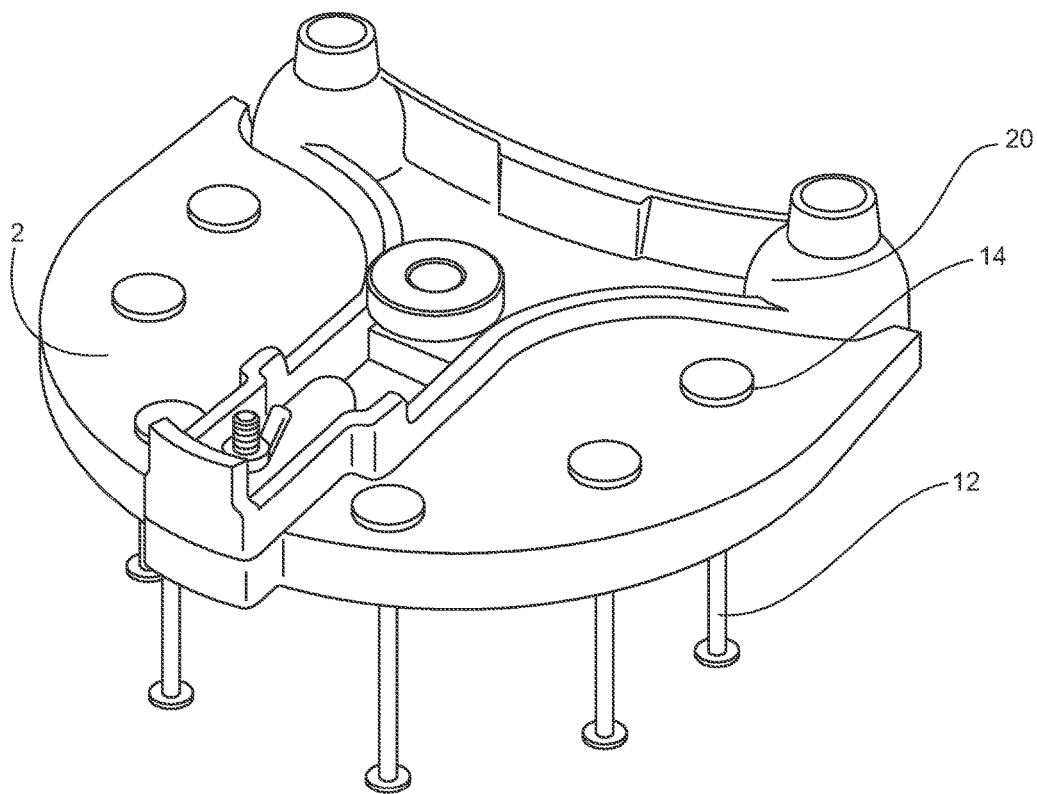

FIG. 4 shows an inverted view of the base of the articulator 20, with magnets 14 used to hold rigid struts 12 in the bores of the positioning jig 2.

Figure 5:
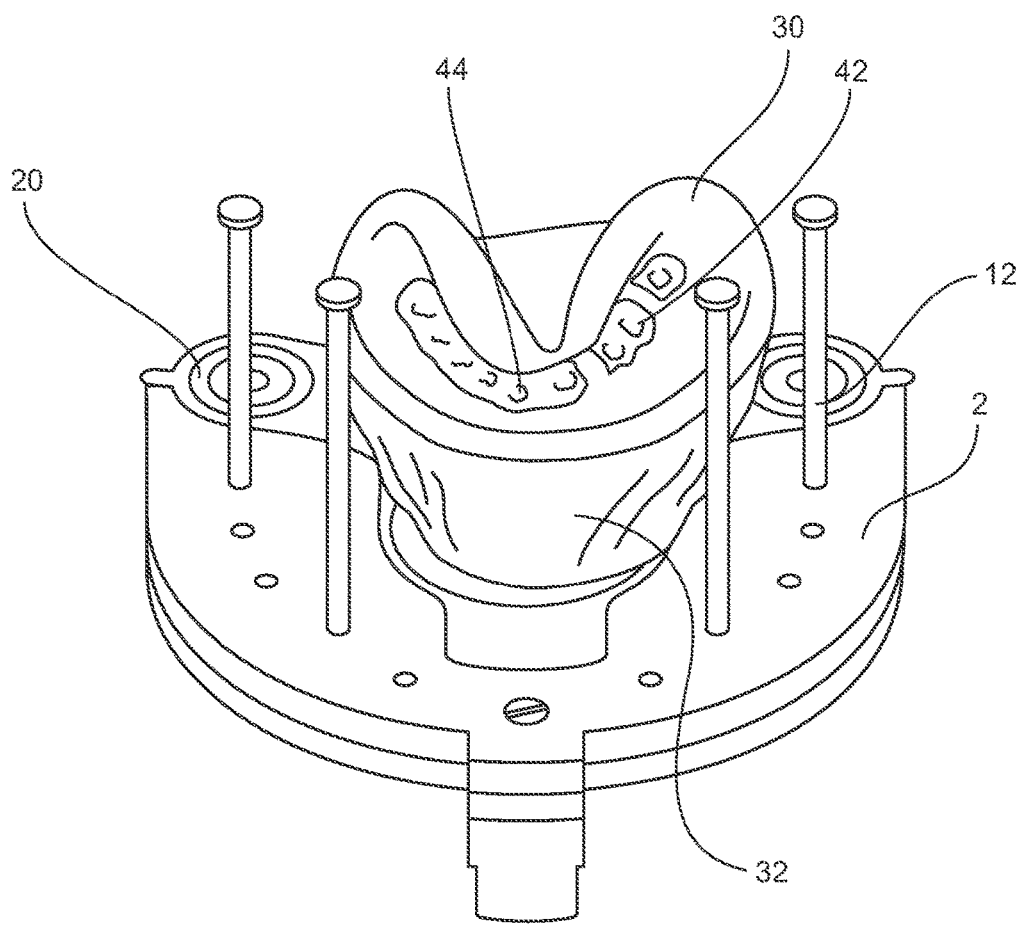

FIG. 5 shows a master cast 30 on a plaster mounting 32 on the articulator 20 with a dental mockup 42 with mockup screws 44. Also shown are the rigid struts 12 in the bores of the positioning jig 2.

Figure 6:
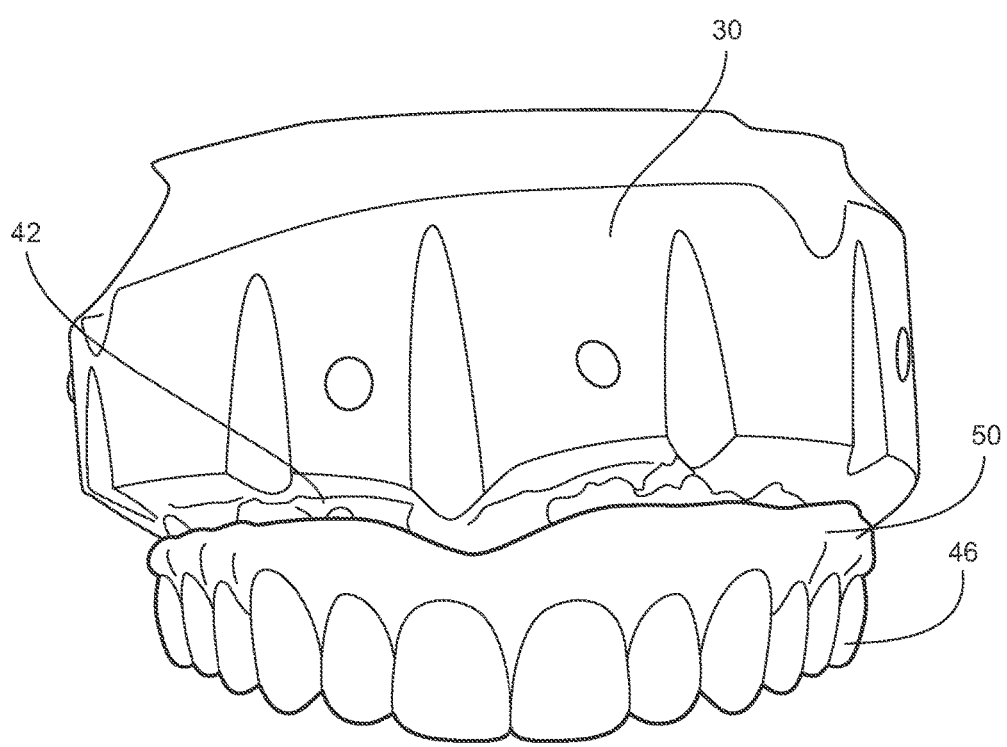

FIG. 6 shows a frontal view of the artificial teeth 46 with a dental bridge 50 and dental mockup 42 mounted on the master cast 30.

Figure 7:
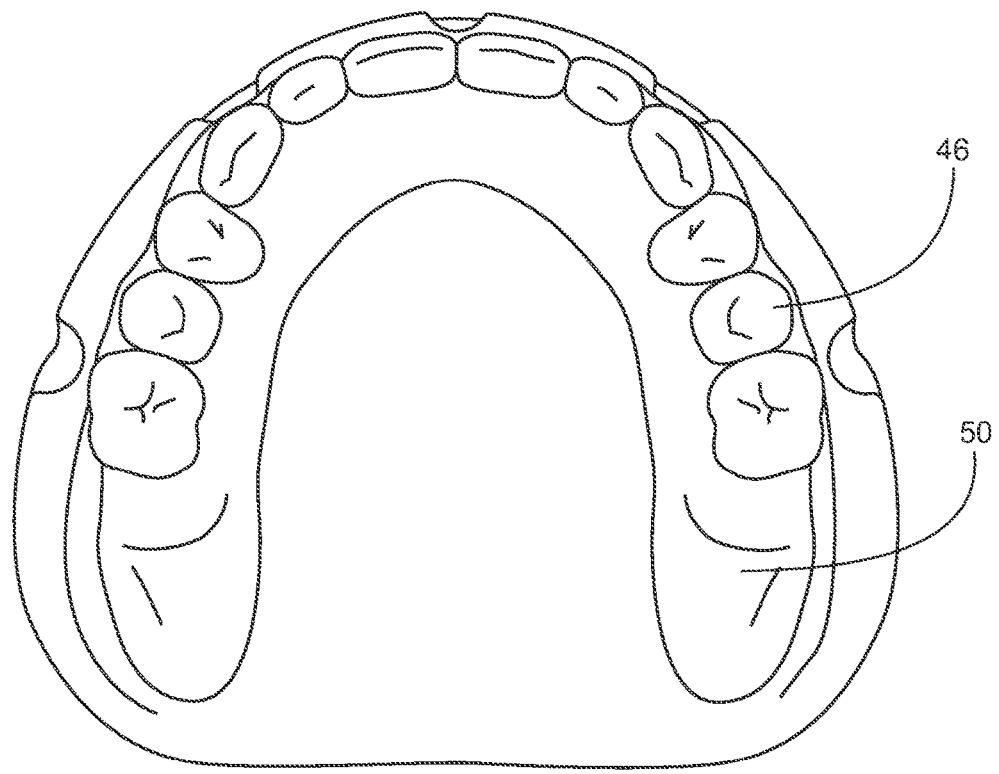

FIG. 7 shows a top view of the artificial teeth 46 with a dental bridge 50.

Figure 8:
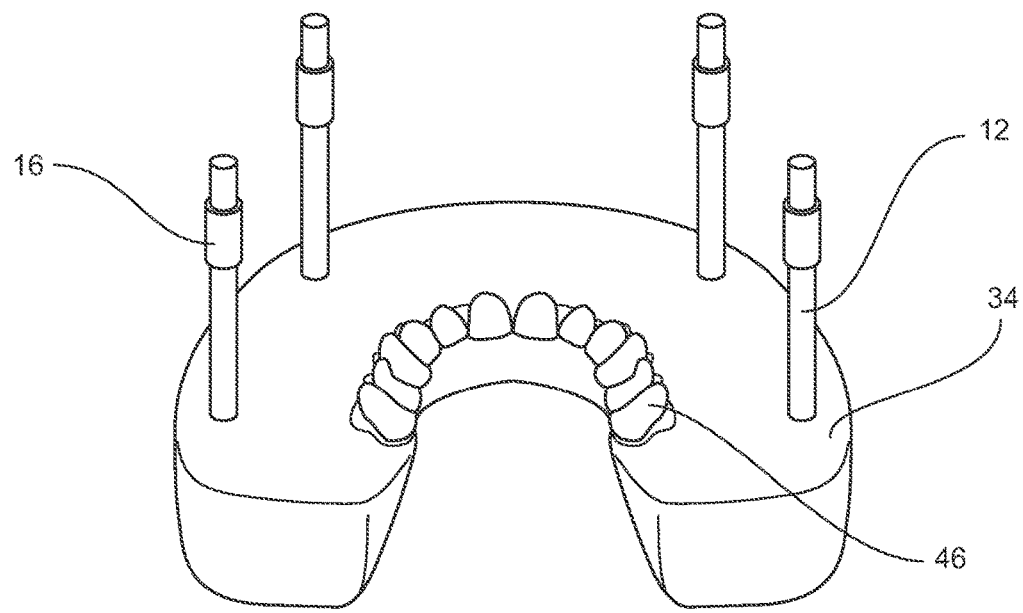

FIG. 8 shows the artificial teeth 46 in an artificial tooth arrangement (ATA) mounted on the stone matrix 34 with rigid struts 12 and shrink wrap tubes 16.

Figure 9:
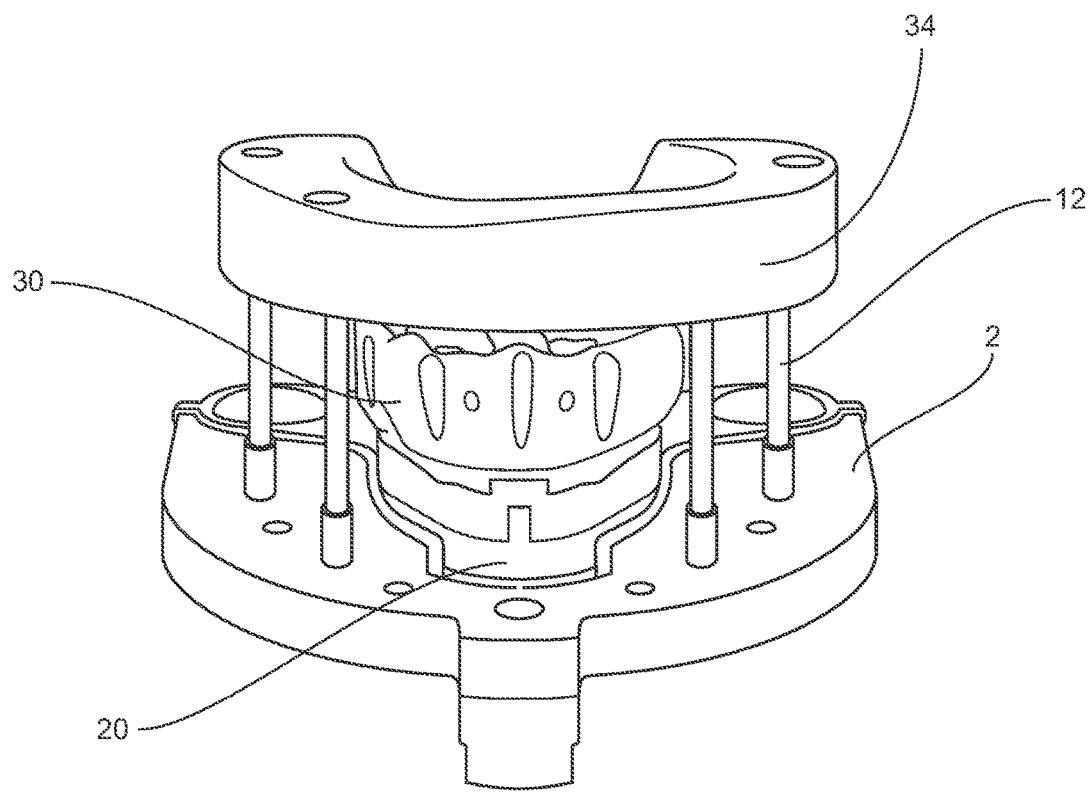

FIG. 9 shows a front view the master cast 30, the stone matrix 34 positioned on the base of the articulator 20 with the positioning jig 2. Also shown are the rigid struts 12.

Figure 10:
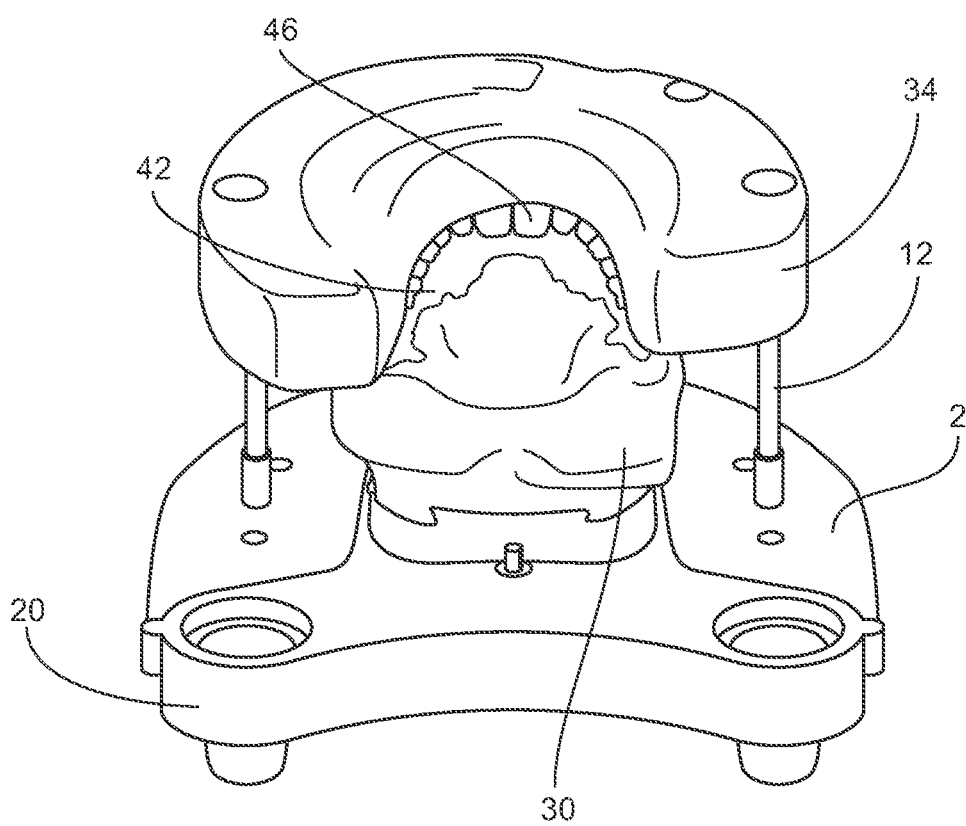

FIG. 10 shows a back view the stone matrix 34, the ATA in place with the master cast 30, dental mockup 42 and artificial teeth 46 mounted on the positioning jig 2 on the base of the articulator 20. Also shown are the rigid struts 12.

Figure 11:
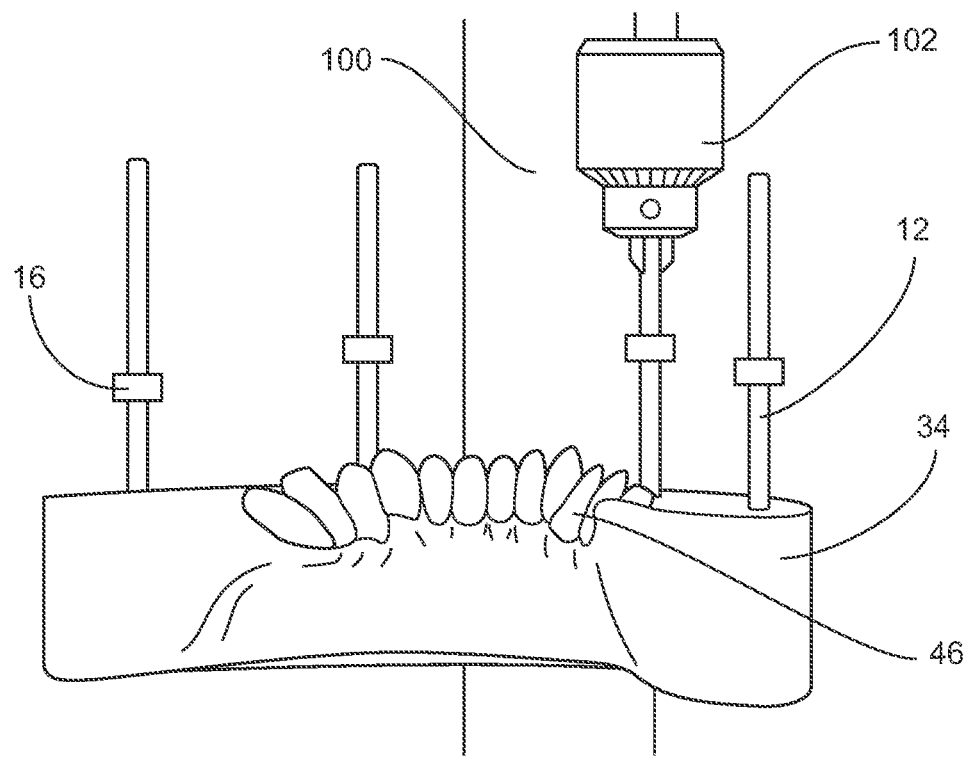

FIG. 11 shows the ATA with teeth 46 in the stone matrix 34 in a drilling press 100 using the drilling chuck 102 and the rigid struts 12 to properly align the ATA to drill the aligned holes. Also shown are the shrink wrap tubes 16 for vertical alignment.

Figure 12:
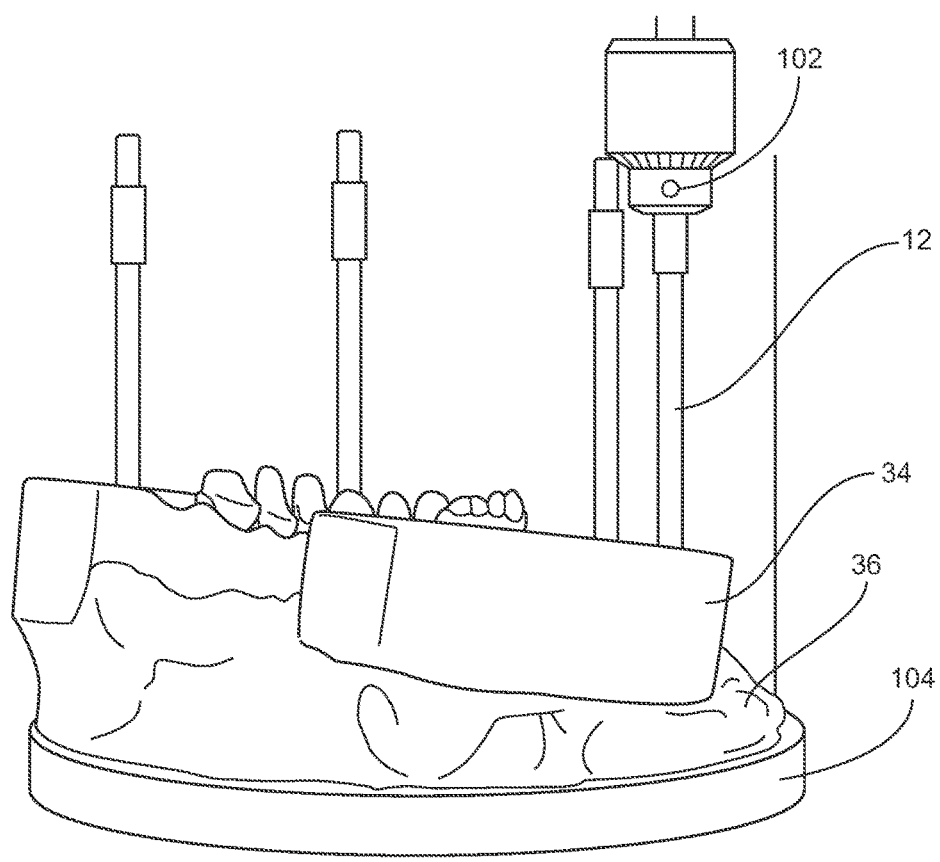

FIG. 12 shows the ATA in the stone matrix 34, the drilling chuck 102, and the rigid struts 12 with an additional mounting stone 36 to stabilize the stone matrix 34 on the drill press table 104.

Figure 13:
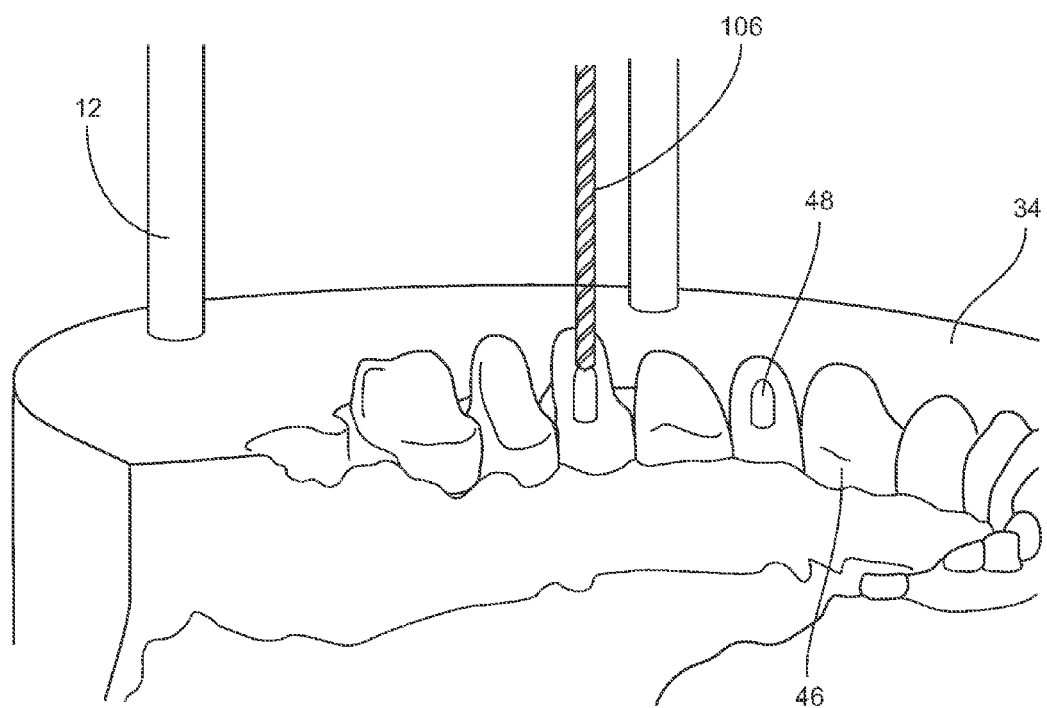

FIG. 13 shows the drill bit 106, drilling aligned holes 48 into the artificial teeth 46 in the ATA mounted on the stone matrix 34 with rigid struts 12.

Figure 14:
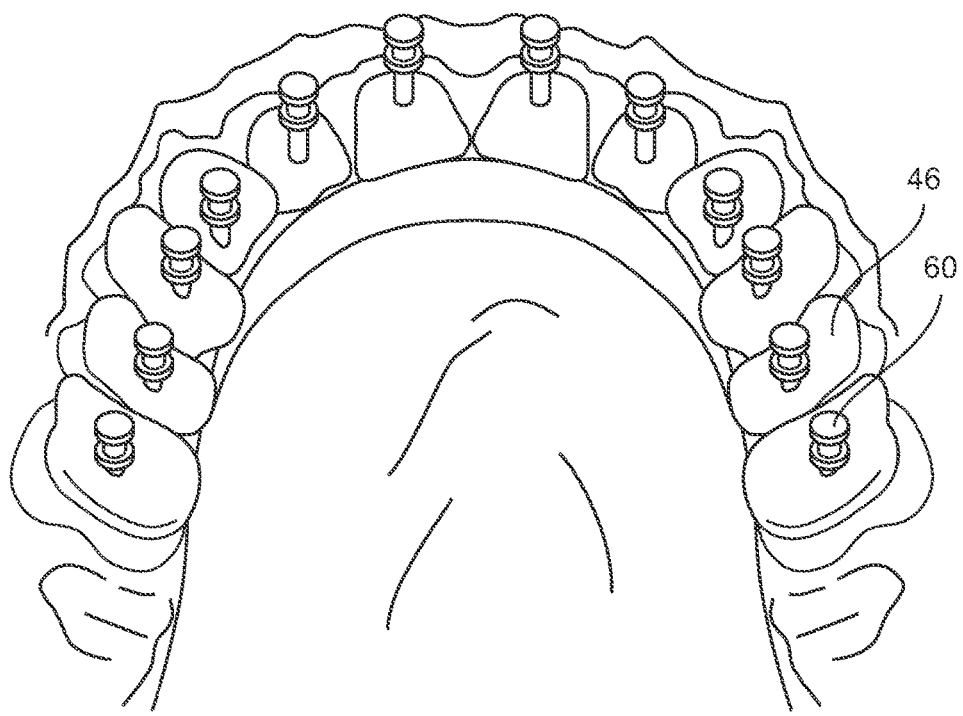

FIG. 14 shows the rods 60 (serrated plastic burnout posts) in the artificial teeth 46 of the ATA.

Figure 15:
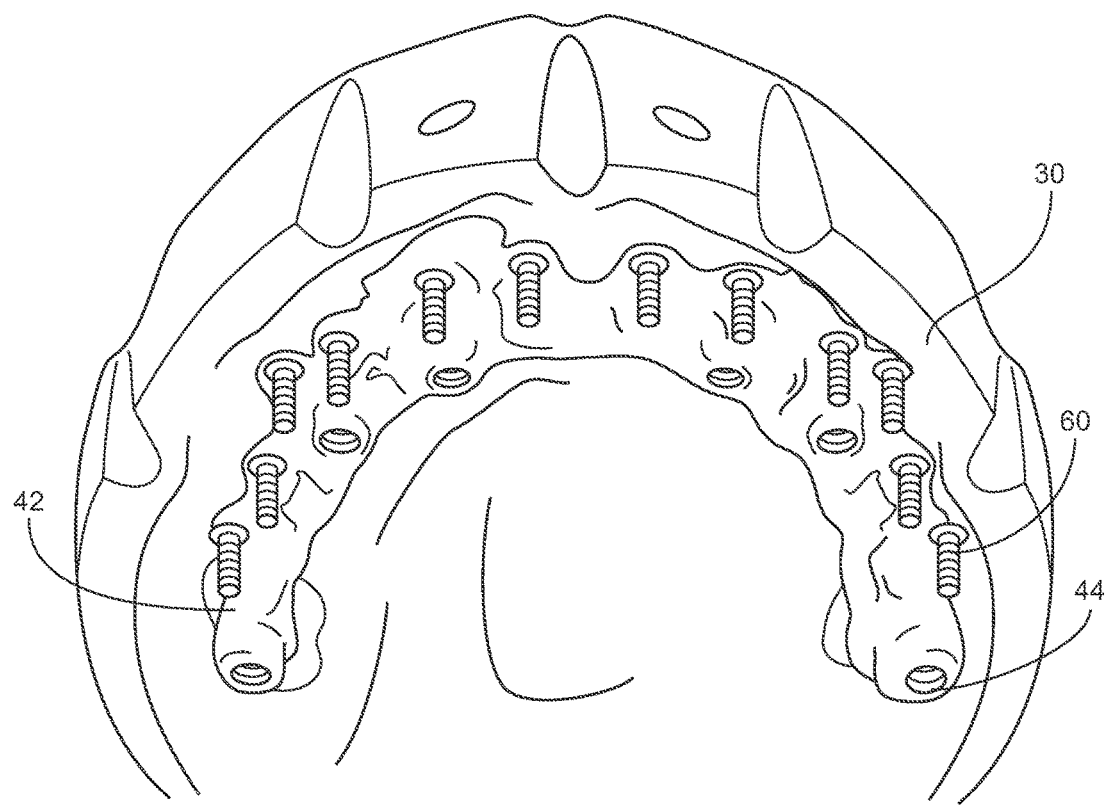

FIG. 15 shows the rods 60 in the dental mockup 42 including screw holes 44 for attachment to implant(s) positioned in the master cast 30.

Figure 16:
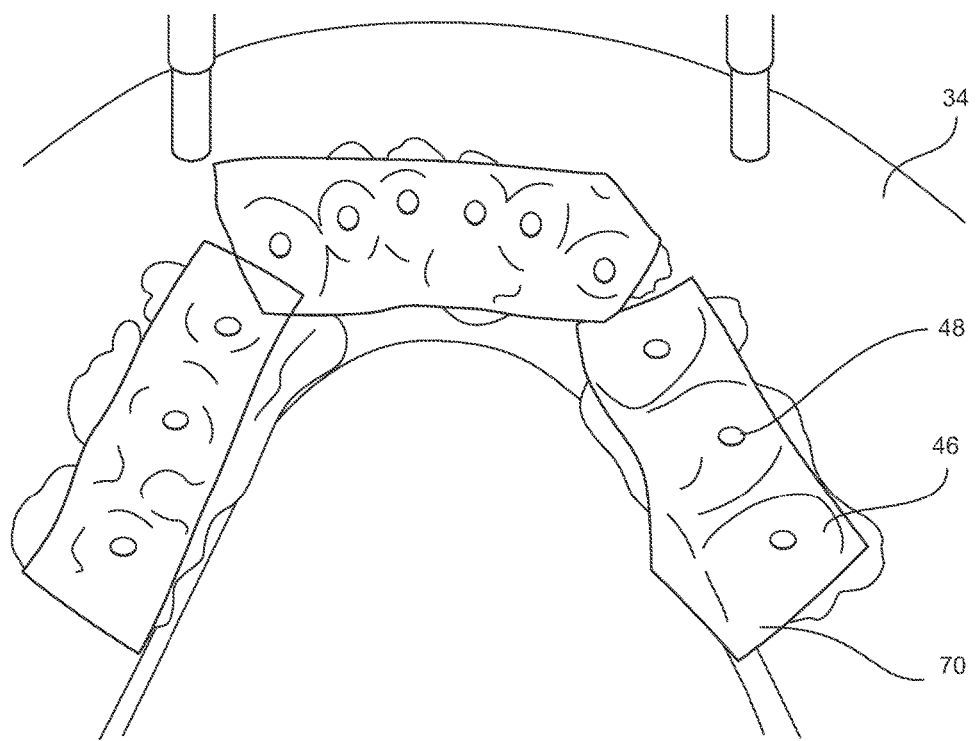

FIG. 16 shows alternative method of preparing a dental mockup using pressure sensitive wax 70 on top of the ATA with holes 48 drilled in the artificial teeth 46 mounted on the stone matrix 34.

Figure 17:
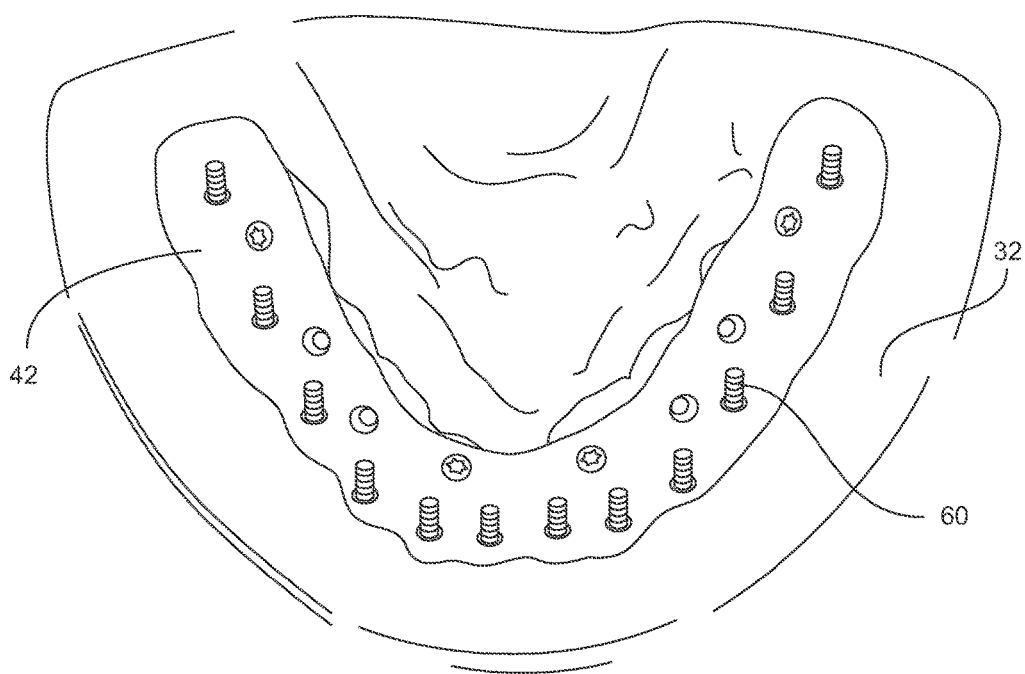

FIG. 17 shows a dental mockup 42 with aligned rods 60 prepared by an alternate method mounted on the master cast 30.

Figure 18:
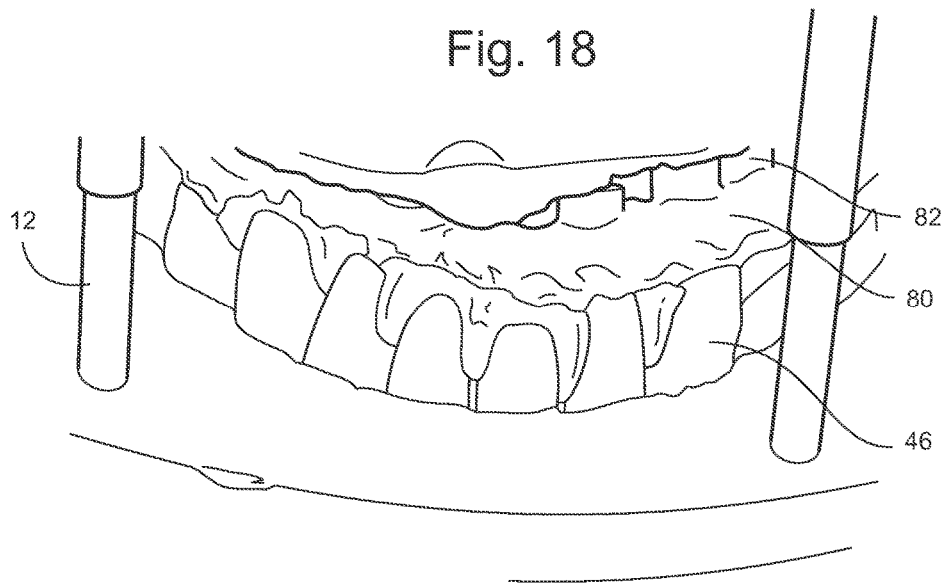

FIG. 18 shows the fabricated metal framework 80 with holes for screws 82 to attach an implant and artificial teeth 46 in the stone matrix with struts 12.

Figure 19:
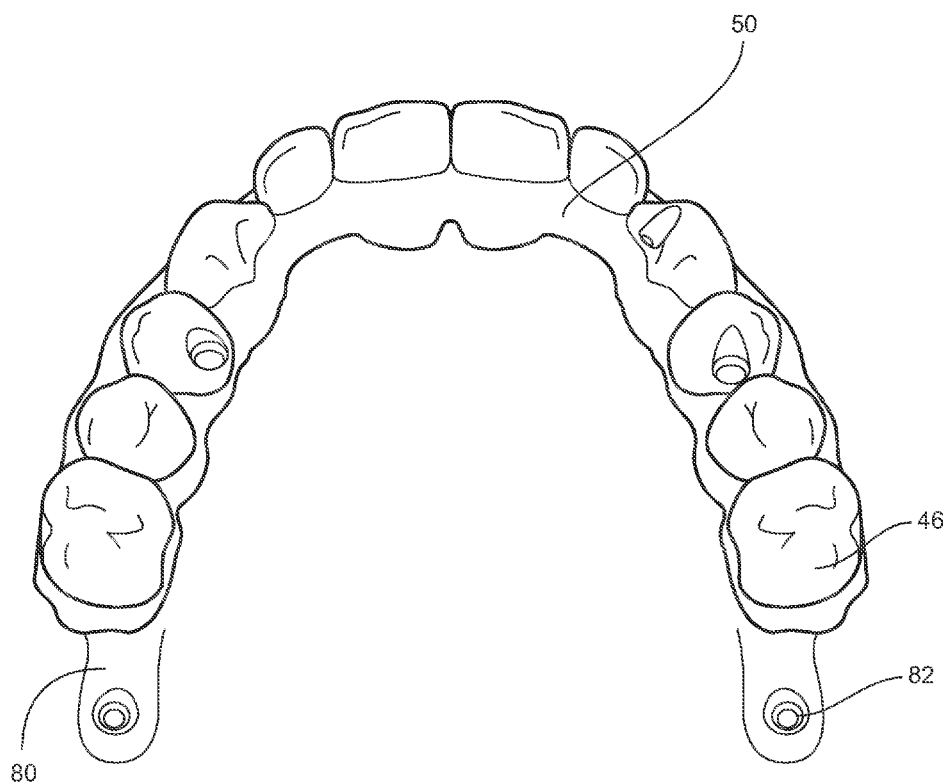

FIG. 19 shows the top view of the artificial teeth 46, dental bridge 50, fabricated metal framework 80 and holes for screws 82.

Figure 20:
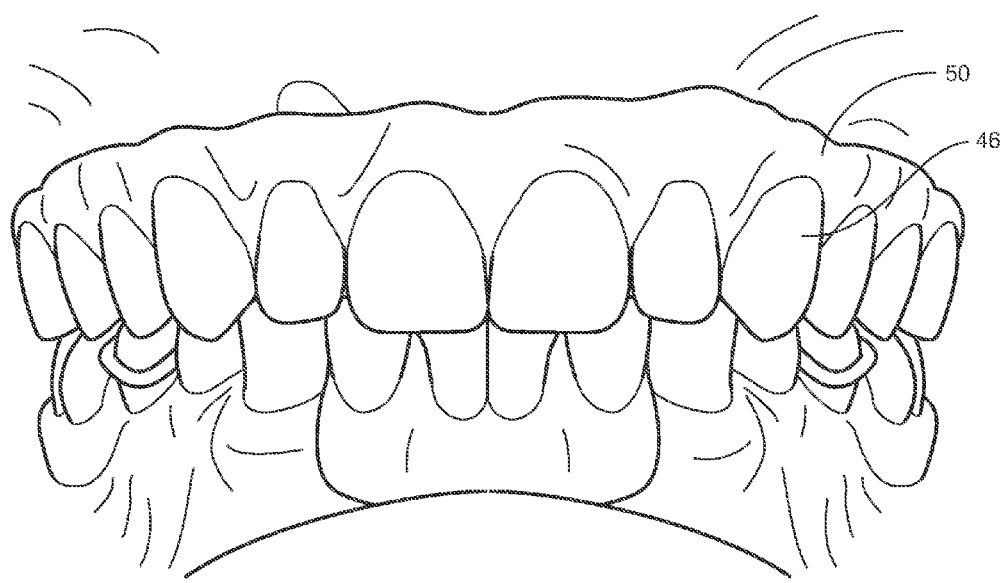

FIG. 20 shows the front view of the artificial teeth 46 and dental bridge 50 in a patient's mouth.

5. DETAILED DESCRIPTION OF THE INVENTION

5.1. Positioning Jigs

The invention provides a positioning jig for preparing two or more adjacent teeth for a dental prosthesis comprising: a member with (i) three or more parallel bores in the member; and (ii) one or more means for attaching the member to a dental articulator. In one embodiment, the member has four or more parallel bores. In another embodiment, the member has six or more parallel bores. In a preferred embodiment, the parallel bores are perpendicular to the plane of the member. In one non-limiting embodiment of the positioning jig, at least three of the parallel bores are of a first diameter and at least three of the parallel bores are of a second diameter. In a non-limiting preferred embodiment, the parallel bores in the member are distributed evenly on either side of the means for attaching to the dental articulator.

The positioning jig may have a means for attaching the member to the dental articulator which may be a screw; a pin and a screw; a plurality of screws; or a clamp.

In the positioning jig, the member may be a plastic frame such as a clear plastic frame. However, the jig may be made of any rigid material, such as plastic, metal, ceramic. In non-limiting embodiments, the jig may be made of clear plastic to aid in visualization. The jig may be made of hard plastic such as Lexan®, Lucite®, Perspex®, Plexiglas®, or polyvinyl chloride (PVC).

In one non-limiting embodiment, the means for attaching the positioning jig to the articulator may be a screw and pin as shown in FIG. 2. Alternatively, the means for attaching the positioning jig to the articulator may be a metal clip or clamp. One of ordinary skill in the art will recognize that there are a variety of ways to hold the positioning jig in place on an articulator.

5.2. Methods of Preparing Artificial Prostheses

The invention provides a method of preparing an artificial prosthesis having two or more adjacent teeth which comprises: preparing an artificial tooth arrangement (ATA) with two or more adjacent teeth in a mold on a positioning jig comprising a member with (i) three or more parallel bores in the member and (ii) one or more means for attaching the member to a dental articulator; placing at least three rigid struts in the parallel bores of the positioning jig; using at least one of the rigid struts to align a drill; drilling an aligned hole into each of the teeth in the mold; placing a rod in each of the aligned holes of the teeth to form a series of aligned rods; using the teeth and the aligned rods to prepare a dental mockup; copying the dental mockup to prepare a dental bridge; and affixing the teeth using the aligned holes to the dental bridge so as to prepare the artificial prosthesis.

In one embodiment of the method, the dental bridge may be acrylic, metal. The artificial prosthesis may be a fixed dental prosthesis, a removable dental prosthesis, a maxillofacial prosthesis, or a fixed detachable prosthesis. The teeth may be porcelain teeth, plastic teeth, or composite teeth.

The artificial tooth arrangement (ATA) may be prepared with three or more adjacent teeth or a full arch of adjacent teeth.

The invention also provides a method of preparing a dental mockup with two or more aligned holes which comprises: preparing an artificial tooth arrangement (ATA) with two or more adjacent teeth in a mold on a positioning jig comprising a member with (i) three or more parallel bores in the member, and (ii) one or more means for attaching the member to a dental articulator; placing at least three rigid struts in the parallel bores of the positioning jig; using at least one of the rigid struts to align a drill; drilling an aligned hole into each of the teeth in the mold; placing a rod in each of the aligned holes of the teeth to form a series of aligned rods; and using the teeth and the aligned rods to prepare the dental mockup with the plurality of aligned holes.

These new methods allow control of the positioning of individual teeth in 3-dimensions and are well-suited to preparation of artificial teeth "en masse" for making prostheses.

In one non-limiting example, the invention provides methods for aligning hardened acrylic teeth in an arrangement set in a heat polymerized acrylic resin supported by a screw-retained metal framework on osseointegrated implants. There are several design considerations for an improved method of making dental implants.

Design considerations for improved implants include: increasing thickness of the veneering materials, the teeth and the heat cured resin; maintaining the denture tooth thickness and not hollowing the teeth out or reducing their surface area; using precious alloys or Titanium or Co—Cr alloys; and improving retentive elements to support the denture teeth. The thickness of the frameworks is critical to prevent fracture. Lastly, one of ordinary skill would recognize that there are many systems for improved bonding of the artificial teeth to metal framework for further retention.

Previously, others have used metal rods to support anterior denture teeth in removable partial denture framework designs and attempts were made to do the same in a hybrid framework. Unfortunately, laboratory technicians found it difficult to wax parallel rods and draw the denture teeth in the same path. Attempts were made to use a verticulator to aid in making parallel rods for individual tooth support. The limited visibility due to the minimal vertical tracking by the verticulator made this means difficult. The cast frames also needed to be soldered and sometimes the soldering would destroy the rods.

In one non-limiting embodiment, the invention provides a method of preparing a denture to be affixed directly to implants, or to multi-unit abutments. In another embodiment, the invention provides a method to prepare an overdenture for attachment to an implant bar. The methods may be used for two artificial teeth, three artificial teeth, four artificial teeth, five artificial teeth, six artificial teeth, seven artificial teeth, eight artificial teeth, nine artificial teeth, ten artificial teeth, eleven artificial teeth, twelve artificial teeth, a partial arch, or a full arch. The teeth may be either in the upper jaw, maxillary, or lower jaw mandibular.

The implants may be from those Branemark System™ with an external hex connection such as those sold by Nobel Biocare (Zurich, Switzerland) under the Branemark™ or NobelSpeedy™ names; an internal conical connection, such as the NobelActive™; or an internal tri-channel connection such as the NobelReplace™ products e.g., Replace™ Select TC NP or RP. Abutments suitable for the invention may be straight or angled and include products such as Snappy™ abutment, GoldAdapt™ abutment, Locator® abutment, or ball abutment. In a non-limiting embodiment, the positioning jig and methods of the invention may be used in all implant systems so long as you have a screw or adhesive retained restoration.

One of ordinary skill would recognize a variety of implant bar products for fixed or removable prostheses. Examples include, but are not limited to, NobelProcera™ implant bar, the Montreal bar, or the wrap-around bar. Other techniques are described by White et al. White Lewis et al., 1992 J Prosth Dent 67(2) 264-268 "Framework Design for Bone-Anchored Fixed Prostheses," the contents of which are hereby incorporated by reference in their entirety. See also the textbook by Branemark, *Tissue-Integrated Prostheses: Osseointegration in Clinical Dentistry* published in 1985 by Quintessence as a basic book on the technique for implants.

5.3. Kits

In another non-limiting embodiment, the invention provides a kit which comprises: a positioning jig for preparing two or more adjacent teeth for a dental prosthesis comprising a member with (i) three or more parallel bores in the member and (ii) one or more means for attaching the member to a dental articulator; and three or more rigid struts with a diameter so they fit tightly in the parallel bores. The kit may have at least three of the parallel bores of a first diameter and at least three of the parallel bores of a second diameter. The kit may contain three or more rigid struts with a diameter so they fit tightly in the parallel bores of the first diameter; and three or more rigid struts having a diameter so they fit tightly in the parallel bores of the second diameter. The kit may further contain a set of shrink wrap tubes with a diameter suitable to fit on the rigid struts. The kit may also contain rigid struts made of a ferrous material and further comprise a set of magnets capable of holding the rigid struts in the bores of the positioning jig. The kit may further comprise a form for casting a mold to support an artificial tooth arrangement (ATA) or one or more drill bits suitable for drilling holes in artificial teeth.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

The following Examples further illustrate the invention and are not intended to limit the scope of the invention.

6. EXAMPLES

To the issues described above concerning dental implants for multiple teeth the solutions were as follows: 1. Simplify the wax-up of the frame; 2. Develop a jig for maintaining tooth position and vertical dimension as well as giving proper physical access for the wax-up and design; and 3. Use CAD-CAM to eliminate soldering and reduce distortion.

Specifically, the layout of dental prosthesis needs to be guided by the patient's existing teeth. These implants are tooth guided and that it is critical to understand tooth positioning before implant placement. The exact positioning of the individual teeth needs to be well understood before the implants are placed. One needs an acceptable artificial tooth arrangement (ATA). Once the ATA has been prepared, one creates a positioning index for the teeth relating them to the implants. The jaw relation records must be accurate. Improperly positioned teeth have temporal and monetary repercussions if the centric relation is incorrect. Then one can design and fabricate a framework leading up to the try-in appointment. Once the try-in is done, one can complete the prosthesis. Once the ATA is completed and signed off by the patient one can begin the process of fabricating the framework.

In one preferred embodiment, the teeth are Phonares NEC (Ivoclar Vivadent AG, Liechtenstein) or Vita Physiodens (Bad Säckingen, Germany) because they have greater bulk at the ridge lap.

The jig needs to maintain tooth position throughout the design process up to the completed prosthesis. FIG. 1 shows the positioning jig 2 with a plurality of bores 4, 6. This PVC attachment was fabricated on a 3-axis milling machine. The bores are of two sizes that allow both maxillary and mandibular casts to be mounted. In one embodiment, the smaller bores 4 were designed for struts based on 2½ inch nails, size 8d and the larger bores 6 were designed for struts based on 3 inch nails, size 10d.

Using an H2 Articulator that was disassembled, the jig was attached to the articulator base as shown in FIG. 2. For more details about dental articulators, see U.S Pat. No. 3,035,350 Franwick, the contents of which are hereby incorporated by reference in its entirety. Specifically, the jig 2 was attached by means of a screw 8 and a pin 10 to the base of the articulator 20. FIG. 3 shows the jig 2 with struts 12 in place. The nails are ground down to remove the points and form the struts 12. This allows the nails to seat into the pre-drilled holes on the tooth positioning jig. A minimum of three nails are needed to tripod the index. There are two preferred ways that Applicant has used for creating the index. One is to keep the jig in the upright position and the other is to invert the jig.

FIG. 4 shows an inverted view of the base of the articulator 20, with magnets 14 used to hold rigid struts 12 in the bores of the positioning jig 2. FIG. 5 shows a master cast 30 on a plaster mounting 32 on the articulator 20 with a dental mockup 42 with mockup screws 44. The methods to make such casts have been described in the literature such as Ivanhoe et al, Ivanhoe et al., 1991, *J Prosth Dent* 66(3) 410-411 "An Impression Technique for Osseointegrating Implants," the contents of which are hereby incorporated by reference in its entirety. FIG. 6 shows a frontal view of the artificial teeth 46 with a dental bridge 50 and dental mockup 42 mounted on the master cast 30. FIG. 7 shows a top view of the artificial teeth 46 with a dental bridge 50.

The tooth positioning jig 2 indexes the exact positions of the artificial teeth 46 so to not have to remove the master casts 30 from their mountings as done previously. This saves time and material. This allows the ATA to be indexed to the cast without the wax and base material in the way. It allows for complete visualization for designing the frame. The jig 2 is designed to maintain tooth position. The jig 2 was designed to fit on the base of an H2 Articulator 20. One skilled in the art could use these teachings to prepare similar jigs for other articular models such as Whip-Mix which manufactures Denar and Hanau Articulators. The casts do not need to be recreated.

One method to create the index on the tooth positioning jig, magnets 14 are placed on the underside of the jig 2 to hold the nails/struts 12 in position as the jig is being turned over. A form is used, that consists of a plastic ring with a clear copyplast material (Biostar-Great Lakes) bottom. Specific areas of the cast are blocked out with putty or play-doh. Stone is poured into the form and the cast on the jig 2 is positioned carefully into the stone 34. The putty or block-out material is removed and the form carefully disengaged. The wax and tray material are removed leaving the artificial teeth 46 embedded in the stone matrix 34. The composite resin base material is also removed. See FIG. 8 with the artificial teeth 46 in indexed artificial tooth arrangement (ATA) mounted on the stone matrix 34 with rigid struts 12. The resulting index has the artificial teeth 46 and one can clearly see the relationship between the teeth and the implants. The stone matrix 34 also gives a flat base that is perpendicular to the nails 12 which is important when creating the retentive rods for the teeth.

Wax can be added to lute the artificial teeth to the stone matrix 34. A glue gun can also be employed to lute the teeth to the stone matrix 34. Shrink wrap 16 is placed on the nails 12 and heated into place with a hand held torch to aid in visualizing any change(s) in vertical dimension(s).

Next, the framework is then designed. GC pattern resin (Alsip, Ill.), a self-curing, general purpose acrylic resin, is used to connect the implants together. The contours of the teeth are taken into account in the buildup of the GC Pattern resin. The design is taking shape and finally one needs to add the teeth. FIG. 9 shows a front view the master cast 30, the stone matrix 34 positioned on the base of the articulator 20 with the positioning jig 2. Also shown are the rigid struts 12. FIG. 10 shows a back view the stone matrix 34, the ATA in place with the master cast 30, dental mockup 42 and artificial teeth 46 mounted on the positioning jig 2 on the base of the articulator 20. Also shown are the rigid struts 12.

Next, the ATA needs to be related to the implants and GC pattern resin of the dental mockup 42. The stone matrix 34 with the embedded teeth 46 are placed on a drill press 100. See FIG. 11. The nails 12 and the Jacob's chuck 102 give the correct angulation for the drill. It is critical that the drill be parallel to the nails to allow for a path of draw. This allows for separation of the components and allows teeth to draw easily in the flask when making the prosthesis.

When the stone matrix is in the Jacob's chuck, a 1 mm Biocryl splint materials is placed on the drill press table 104. An additional mounting stone 36 is used to stabilize the stone matrix 34 on the drill press table 104. The biocryl splint material allows for the ease of movement as it reduces friction between the stone matrix and metal table. Once the mounting stone 36 is set, the nail 12 is released from the Jacob's chuck 102. Now, as shown in FIG. 13, one can drill aligned vertical post holes 48 in each individual tooth 46. In one, non-limiting embodiment, a preferred drill is the parapost drill (Coltene/Whaledent, Cayahoga Falls, Ohio). One places the parapost drill in the chuck and makes sure that the drill is not spinning eccentrically. The black and green parapost drills are too large for most teeth but they are perfect to drill these holes in denture teeth. The red parapost drills work nicely in the lower anterior teeth. Paraposts are widely available and have corresponding plastic serrated posts 60 that can be placed in the holes 48. See FIG. 14.

Once all the holes are drilled, serrated plastic burnout posts 60 are placed into the teeth 46. One makes sure to have clearance for them with the GC pattern resin. One may need to cut back the GC pattern resin or the posts to allow the index to fully seat. The nails 12 with the shrink wrap 16 will indicate if you are not fully seated. Once fully seated, the posts 60 are attached via GC pattern resin to the frame/dental mockup 42. See FIG. 15. It is best to do this "en masse". Once this is done, further refining of the frame/dental mockup may be done. One may wish attach one or more of the teeth to the frame/dental mockup with the GC pattern resin for scanning so as to generate metal replacement for one or more of the artificial teeth. This may be desirable if the corresponding upper or lower teeth are metal so you can have metal-metal contacts on the occlusal surface. One might desire such a framework with some of the teeth metal for the back (posterior) teeth or molars.

An alternative method to practice the invention is using composite resin. As shown in FIG. 16 pressure sensitive wax 70 is placed on the denture teeth 46 to act as a spacer for future acrylic resin. The holes are drilled as described above and then the serrated plastic paraposts 60 are placed in position. A composite resin (Triad) sheet is placed on the master cast 30 allotting for the implants and then the excess is trimmed. A small dab of liquid Triad composite is placed on the post and then the stone index is placed back into the jig and then placed in a light curing vessel. After curing, the index is separated from the jig. The resultant design can be modified or adjusted as needed. Using either method, one creates a dental mockup 42 with posts 60, ready to be copy milled to fabricate a final framework.

In non-limiting embodiments, there are two preferred materials for the framework. One framework material is Grade 4 Pure Titanium which has excellent biocompatibility; a high resistance to corrosion; is light in weight (4 times lighter than gold); and a high polish. Another preferred material is Cobalt Chrome Alloy which also has excellent biocompatibility; high resistance to corrosion; bonds well with Ceramco porcelains; and has low thermal conductivity. A non-limiting preferred method to prepare the framework is CAD/CAM copy milling from the dental mockup. This method has a number of advantages: superior strength of a one-piece design; no casting; no need for laser welding or soldered joints; state of the art milling precludes expansion related distortions and crack formations; and lower cost of fabrication.

The framework is fabricated from a prepared cast with implant analogues. It should include a removable gingival mask and the design to be copy milled. One should also include a verification jig to assure proper fitting in the patient.

One preferred source for the framework fabrication is 3D white light interferometry. Specifically, the design was scanned at the Dentsply Facility at York, Pa. The scanner was designed in Switzerland. Two video cameras are located above and scan the cast or pattern three times. The machine is calibrated daily. The scan is sent via email to Belgium for the actual milling of the framework. Imetric photogrammetry systems employ the basic principle of triangulation, whereby intersecting lines in space are used to compute the location of points and surfaces in all three dimensions. Structured light 3D scanners project a pattern of light on the subject and look at the deformation of the pattern on the subject. The advantage of Imetric structured light 3D scanners over other scanning systems is data quality, precision and speed. These scanners are more accurate than laser scanners with an accuracy on the order of a single nanometer.

Instead of scanning one point at a time, structured light scanners scan multiple points or the entire field of view at once. Capture rate is a fraction of a second. Millions of measurements are made per scan.

The copy milled framework is inspected and upon receipt and the teeth fitted to the frame as they were indexed according to the ATA. The framework is then tried in the mouth. The teeth can then be added at the same visit for a final try-in at the same visit. FIG. 18 shows the fabricated metal framework 80 and artificial teeth 46 in the stone matrix 34. FIG. 19 shows the top view of the artificial teeth 46, dental bridge 50, fabricated metal framework 80 and holes for screws 82 to attach the hybrid prosthesis to the osseointegrating implants. FIG. 20 shows the front view of the artificial teeth 46 dental bridge 50 and fabricated metal framework 80 in a patient's mouth.

One of skill in the art will understand that the positioning jig and methods described herein are applicable to other fixed denture designs.

Completing the Prosthesis

Since beads are not placed on the framework, bonding to the frame is necessary. There are several metal-resin bonding systems designed to improve bond strength and decrease microleakage at the resin-metal interface, including Silicoater MD, Rocatec, and Kevioc. One of ordinary skill would readily recognize a variety of suitable materials for bonding composite, plastic, resin or ceramic teeth to the metal framework.

Flashing and Processing

One may flask and process the denture in the classical way. One needs to be sure to allow for the flask to draw in the same path of the metal rods. One can make the holes in the teeth slightly larger if needed to allow heat cured acrylic to flow in those areas for retention. In one non-limiting embodiment, Teflon rope is used to maintain the screw holes during processing.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application was specifically and individually indicated to be incorporated by reference.

What is claimed is:

1. A method of preparing an artificial prosthesis having two or more adjacent teeth which comprises:
   (a) preparing an artificial tooth arrangement (ATA) with two or more adjacent teeth in a mold on a positioning jig comprising a member with (i) three or more parallel bores in the member and (ii) one or more means for attaching the member to a dental articulator;
   (b) placing at least three rigid struts in the parallel bores of the positioning jig;
   (c) using at least one of the rigid struts to align a drill;
   (d) drilling an aligned hole into each of the teeth in the mold;
   (e) placing a rod in each of the aligned holes of the teeth to form a series of aligned rods;
   (f) using the teeth and the aligned rods to prepare a dental mockup;
   (g) copying the dental mockup to prepare a dental bridge; and
   (h) affixing the teeth using the aligned holes to the dental bridge so as to prepare the artificial prosthesis.

2. The method of claim 1, wherein the dental bridge is acrylic.

3. The method of claim 1, wherein the dental bridge is metal.

4. The method of claim 1, wherein the artificial prosthesis is a fixed dental prosthesis.

5. The method of claim 1, wherein the artificial prosthesis is a removable dental prosthesis.

6. The method of claim 4, wherein the fixed dental prosthesis is a maxillofacial prosthesis.

7. The method of claim 1, wherein the artificial prosthesis is a fixed detachable prosthesis.

8. The method of claim 1, wherein the teeth are porcelain teeth.

9. The method of claim 1, wherein the teeth are plastic teeth.

10. The method of claim 1, wherein the teeth are composite teeth.

11. The method of claim 1, wherein the artificial tooth arrangement (ATA) is prepared with three or more adjacent teeth.

12. The method of claim 11, wherein the artificial tooth arrangement (ATA) is prepared with a full arch of adjacent teeth.

13. The method of claim 1, wherein the member of the positioning jig has four or more parallel bores.

14. The method of claim 1, wherein the member of the positioning jig has six or more parallel bores.

15. The method of claim 14, wherein at least three of the parallel bores of the member of the positioning jig are of a first diameter and at least three of the parallel bores are of a second diameter.

16. The method of claim 1, wherein the parallel bores are perpendicular to the plane of the member of the positioning jig.

17. A method of preparing a dental mockup with two or more aligned holes which comprises:
- (a) preparing an artificial tooth arrangement (ATA) with two or more adjacent teeth in a mold on a positioning jig comprising a member with (i) three or more parallel bores in the member, and (ii) one or more means for attaching the member to a dental articulator;
- (b) placing at least three rigid struts in the parallel bores of the positioning jig;
- (c) using at least one of the rigid struts to align a drill;
- (d) drilling an aligned hole into each of the teeth in the mold;
- (e) placing a rod in each of the aligned holes of the teeth to form a series of aligned rods; and
- (f) using the teeth and the aligned rods to prepare the dental mockup with the plurality of aligned holes.

18. The method of claim 17, wherein the member of the positioning jig has six or more parallel bores.

19. The method of claim 18, wherein at least three of the parallel bores of the member of the positioning jig are of a first diameter and at least three of the parallel bores are of a second diameter.

20. The method of claim 17, wherein the parallel bores are perpendicular to the plane of the member of the positioning jig.

* * * * *